(12) United States Patent
Srinivasan et al.

(10) Patent No.: US 8,751,261 B2
(45) Date of Patent: Jun. 10, 2014

(54) METHOD AND SYSTEM FOR SELECTION OF PATIENTS TO RECEIVE A MEDICAL DEVICE

(75) Inventors: Soundararajan Srinivasan, Mountain View, CA (US); Alireza Farhangfar, Menlo Park, CA (US)

(73) Assignee: Robert Bosch GmbH, Stuttgart (DE)

(*) Notice: Subject to any disclaimer, the term of this patent is extended or adjusted under 35 U.S.C. 154(b) by 384 days.

(21) Appl. No.: 13/296,788

(22) Filed: Nov. 15, 2011

(65) Prior Publication Data
US 2013/0124224 A1    May 16, 2013

(51) Int. Cl.
G06Q 10/00    (2012.01)
G06Q 50/00    (2012.01)
G06Q 40/00    (2012.01)

(52) U.S. Cl.
USPC .......................................... 705/2; 705/3; 705/4

(58) Field of Classification Search
USPC ........................................................... 705/2–4
See application file for complete search history.

(56) References Cited

U.S. PATENT DOCUMENTS

| | | | |
|---|---|---|---|
| 6,235,474 B1 | 5/2001 | Feinberg | |
| 6,438,407 B1 | 8/2002 | Ousdigian et al. | |
| 6,443,890 B1 | 9/2002 | Schulze et al. | |
| 6,764,447 B2 | 7/2004 | Iliff | |
| 6,803,195 B1 | 10/2004 | Avivi et al. | |
| 7,368,233 B2 | 5/2008 | Shuber et al. | |
| 7,468,032 B2 | 12/2008 | Stahmann et al. | |
| 7,611,870 B2 | 11/2009 | Feinberg | |
| 7,653,556 B2 | 1/2010 | Rovinelli et al. | |
| 7,685,005 B2 | 3/2010 | Riff et al. | |
| 7,811,757 B2 | 10/2010 | Shuber | |
| 7,818,185 B2 | 10/2010 | Bjorner et al. | |
| 7,917,438 B2 | 3/2011 | Kenedy et al. | |
| 7,953,614 B1 | 5/2011 | Reicher et al. | |
| 7,959,568 B2 | 6/2011 | Stahmann et al. | |
| 8,548,937 B2 * | 10/2013 | Saigal et al. ................... 706/52 |
| 2002/0010597 A1 | 1/2002 | Mayer et al. | |
| 2002/0169636 A1 | 11/2002 | Eggers et al. | |
| 2002/0184050 A1 * | 12/2002 | Papageorge ..................... 705/2 |
| 2002/0194032 A1 | 12/2002 | Mankopf et al. | |
| 2003/0009354 A1 * | 1/2003 | Arbogast et al. ................. 705/2 |
| 2003/0065241 A1 | 4/2003 | Hohnloser | |
| 2004/0045560 A1 | 3/2004 | Kent et al. | |
| 2004/0078232 A1 | 4/2004 | Troiani | |
| 2004/0103001 A1 | 5/2004 | Mazar et al. | |

(Continued)

OTHER PUBLICATIONS

International Search Report and Written Opinion in corresponding PCT application (i.e., PCT/US2012/064755), mailed Jun. 10, 2013 (9 pages).

(Continued)

Primary Examiner — Joseph Burgess
(74) Attorney, Agent, or Firm — Maginot, Moore & Beck (57) ABSTRACT

In one embodiment, a method for identifying patients to receive a medical device has been developed. The method includes retrieving first medical data associated with one patient from a database, identifying a probability that a medical device provides a medical benefit to the one patient that exceeds a cost associated with providing the medical device to the one patient with reference to the first medical data and a probabilistic model, the probabilistic model having a plurality of model parameters, each model parameter corresponding to one type of datum in the first medical data, and providing the medical device to the one patient in response to the identified probability exceeding a first predetermined threshold.

18 Claims, 6 Drawing Sheets

(56) References Cited

U.S. PATENT DOCUMENTS

| | | |
|---|---|---|
| 2004/0267570 A1 | 12/2004 | Becker |
| 2006/0111941 A1 | 5/2006 | Blom |
| 2006/0122864 A1 | 6/2006 | Gottesman et al. |
| 2006/0200010 A1 | 9/2006 | Rosales et al. |
| 2006/0206011 A1 | 9/2006 | Higgins et al. |
| 2006/0218007 A1 | 9/2006 | Bjorner et al. |
| 2006/0235280 A1 | 10/2006 | Vonk et al. |
| 2007/0063850 A1 | 3/2007 | Devaul et al. |
| 2007/0136115 A1 | 6/2007 | Senturk Doganaksoy et al. |
| 2008/0133275 A1 | 6/2008 | Haug et al. |
| 2008/0262873 A1 | 10/2008 | Bayne et al. |
| 2009/0105550 A1 | 4/2009 | Rothman et al. |
| 2009/0125325 A1 | 5/2009 | Martinez et al. |
| 2009/0187082 A1 | 7/2009 | Cuddihy et al. |
| 2009/0192826 A1 | 7/2009 | deLusignan et al. |
| 2009/0326981 A1 | 12/2009 | Karkanias et al. |
| 2010/0017231 A1 | 1/2010 | Galbraith et al. |
| 2010/0063840 A1 | 3/2010 | Hoyme et al. |
| 2010/0063930 A1 | 3/2010 | Kenedy et al. |
| 2010/0065840 A1 | 3/2010 | Yamazaki et al. |
| 2010/0131434 A1 | 5/2010 | Magent et al. |
| 2010/0138199 A1 | 6/2010 | Soto et al. |
| 2010/0145953 A1 | 6/2010 | Charles et al. |
| 2010/0204920 A1 | 8/2010 | Dranitsaris et al. |
| 2010/0235178 A1 | 9/2010 | Firminger et al. |
| 2011/0071363 A1 | 3/2011 | Montijo et al. |
| 2011/0092825 A1 | 4/2011 | Gopinathan et al. |
| 2012/0016690 A1* | 1/2012 | Ramarajan et al. ............... 705/2 |

OTHER PUBLICATIONS

Lin et al, "Rationing of Resources: Ethical Issues in Disasters and Epidemic Situations," Prehospital and Disaster Medicine, May-Jun. 2009, pp. 215-221, USA (7 pages).

Mitchell, Tom M., "Generative and Discriminative Classifiers: Naive Bayes and Logistic Regression", Draft article for textbook "Machine Learning" T.M. Mitchell, McGraw Hill, 2010 (17 pages).

* cited by examiner

| PATIENT ID | AGE | SEX | HEIGHT (cm) | WEIGHT (Kg) | WEIGHT TREND (Kg/year) | ... | COST FOR PROVIDING & OPERATING DEVICE | MEASURED BENEFIT FROM DEVICE USE | NET BENEFIT FROM DEVICE? |
|---|---|---|---|---|---|---|---|---|---|
| 1234 | 49 | M | 170 | 82 | +5 | ... | $2100 | $3000 | YES |
| 3452 | 83 | F | 140 | 61 | +2 | ... | $2000 | $500 | NO |
| 6880 | 67 | M | 190 | 87 | -3 | ... | $800 | $800 | UNSURE |
| 3901 | 55 | F | 152 | 53 | -2 | ... | $4200 | $9000 | YES |

FIG. 5

| PATIENT IDENTIFIER | DATE | AGE | SEX | HEIGHT (cm) | WEIGHT (Kg) | ... |
|---|---|---|---|---|---|---|
| 1234 | 2004-06-03 | 47 | M | 170 | 75 | ... |
| 1234 | 2004-09-05 | 47 | M | 170 | 73 | ... |
| 1234 | 2005-06-17 | 48 | M | — | 77 | ... |
| 1234 | 2006-07-01 | 49 | M | 170 | 82 | ... |

FIG. 6

FIG. 7

METHOD AND SYSTEM FOR SELECTION OF PATIENTS TO RECEIVE A MEDICAL DEVICE

TECHNICAL FIELD

This patent relates generally to the fields of medical information and patient management, and, more particularly, to methods and systems for providing medical devices to patients.

BACKGROUND

The fields of telemedicine and home healthcare have experienced strong growth in recent years. In a telemedicine system, a patient is geographically removed from the presence of a doctor or other healthcare provider. For example, the patient could be at home instead of on site at a healthcare facility. Telemedical devices enable the healthcare provider to monitor the health status of a patient and potentially diagnose and treat some medical problems without the need for the patient to travel to the healthcare facility. The use of telemedical systems has the potential to reduce the cost of healthcare, and to improve the quality of healthcare through increased patient monitoring.

Various known telemedicine systems provide a device to a patient that enables the patient to transmit medical data to a doctor or healthcare provider. Some devices are configured to record biosignals, such as heart rate, blood pressure, and respiration rates, and transmit data of the recorded biosignals to a database for later review. Other telemedicine systems enable remote visits between a patient and a healthcare provider and also provide real time medical data to the provider during the visits.

While telemedicine systems have numerous potential advantages, such systems can also present challenges to the healthcare system. Telemedicine systems can increase healthcare costs in at least two different ways. First, the purchase and maintenance costs of the telemedical devices and associated communication infrastructure to support telemedicine contribute to the overall cost of telemedicine systems. Secondly, the amount of time that medical professionals spend analyzing medical data from telemedicine systems contributes to the cost of the telemedicine system and may take away resources from other medical services. Depending upon the medical condition of a patient, a telemedicine system may provide limited additional medical benefit in comparison to traditional treatments. However, when used appropriately, a telemedicine system can reduce the total cost of healthcare and improve the quality of healthcare for many patients. Existing telemedicine systems are, however, not well equipped to identify the patients that are most suitable to receive telemedicine treatment. Thus, improvements to medical systems that help identify patients for telemedical devices would be beneficial.

SUMMARY

In one embodiment, a method for selecting recipients for a medical device has been developed. The method includes providing first medical data associated with one patient from a database stored in a memory to a controller communicatively coupled to the memory, identifying with the controller a probability that a medical device provides a medical benefit to the one patient that exceeds a cost associated with providing the medical device to the one patient with reference to the first medical data and a probabilistic model, the probabilistic model having a plurality of model parameters stored in the memory and provided to the controller, each model parameter corresponding to one type of datum in the first medical data, and generating with a user interface device that is communicatively coupled to the controller an output indicating the one patient is eligible to receive the medical device, the output being generated in response to the identified probability exceeding a first predetermined probability threshold value stored in the memory.

In another embodiment, a system for controlling distribution of medical devices to patients has been developed. The system includes a user interface device, a memory, and a controller operatively connected to the user interface device and the memory. The memory is configured to store a database containing medical data corresponding to a plurality of patients, a plurality model parameters corresponding to a probabilistic model, each model parameter corresponding to one type of datum in the plurality of medical data, and a plurality of stored program instructions. The controller is configured to execute the stored program instructions to retrieve first medical data corresponding to one patient from the database, identify a probability that a medical device provides a medical benefit to the one patient that exceeds a cost associated with providing the medical device to the one patient with reference to the first medical data and the probabilistic model having the plurality of model parameters, and display an output via the user interface device to indicate provision of the medical device to the one patient in response to the identified probability exceeding a first predetermined threshold.

DETAILED DESCRIPTION

For the purposes of promoting an understanding of the principles of the embodiments described herein, reference is now be made to the drawings and descriptions in the following written specification. No limitation to the scope of the subject matter is intended by the references. This patent also includes any alterations and modifications to the illustrated embodiments and includes further applications of the principles of the described embodiments as would normally occur to one skilled in the art to which this document pertains.

The term "telemedicine" as used herein refers to a form of medicine in which a patient and healthcare provider electronically communicate with one other to enable the patient, who is not located in the healthcare provider's facility, to receive medical treatment from the healthcare provider. The term "telemedical device" as used herein refers to any device that is configured to electronically transmit and/or receive data pertaining to a telemedicine treatment received by a patient from a healthcare provider practicing telemedicine on the patient. A telemedical device is one example of a more general category of medical devices, which include any device having diagnostic and/or therapeutic uses, such as respirators, pace makers, blood sugar testing devices, inhalators, heart monitors, and the like. While the specific embodiments described herein are directed to telemedical devices, the systems and methods described herein are also suitable for use with a wide variety of medical devices.

The term "probabilistic model" as used herein refers to a mathematical model that generates a probability value for an event when provided with input data. For example, a probabilistic model generates a probability value when provided with medical data corresponding to the patient. The term "medical data" as used herein refers to any data relevant to medical treatment of a patient. The term "medical record" refers to a set of medical data corresponding to a patient. The probability value generated by a probabilistic model described in this document indicates the likelihood that the selected patient will experience a benefit that outweighs a corresponding cost if provided with a telemedical device. Some embodiments of probabilistic models discussed in this document include parameters that are associated with medical data for the patient. As described below, the values of the parameters provided to the probabilistic model are generated using collected medical data for one or more patients.

Figure 1:
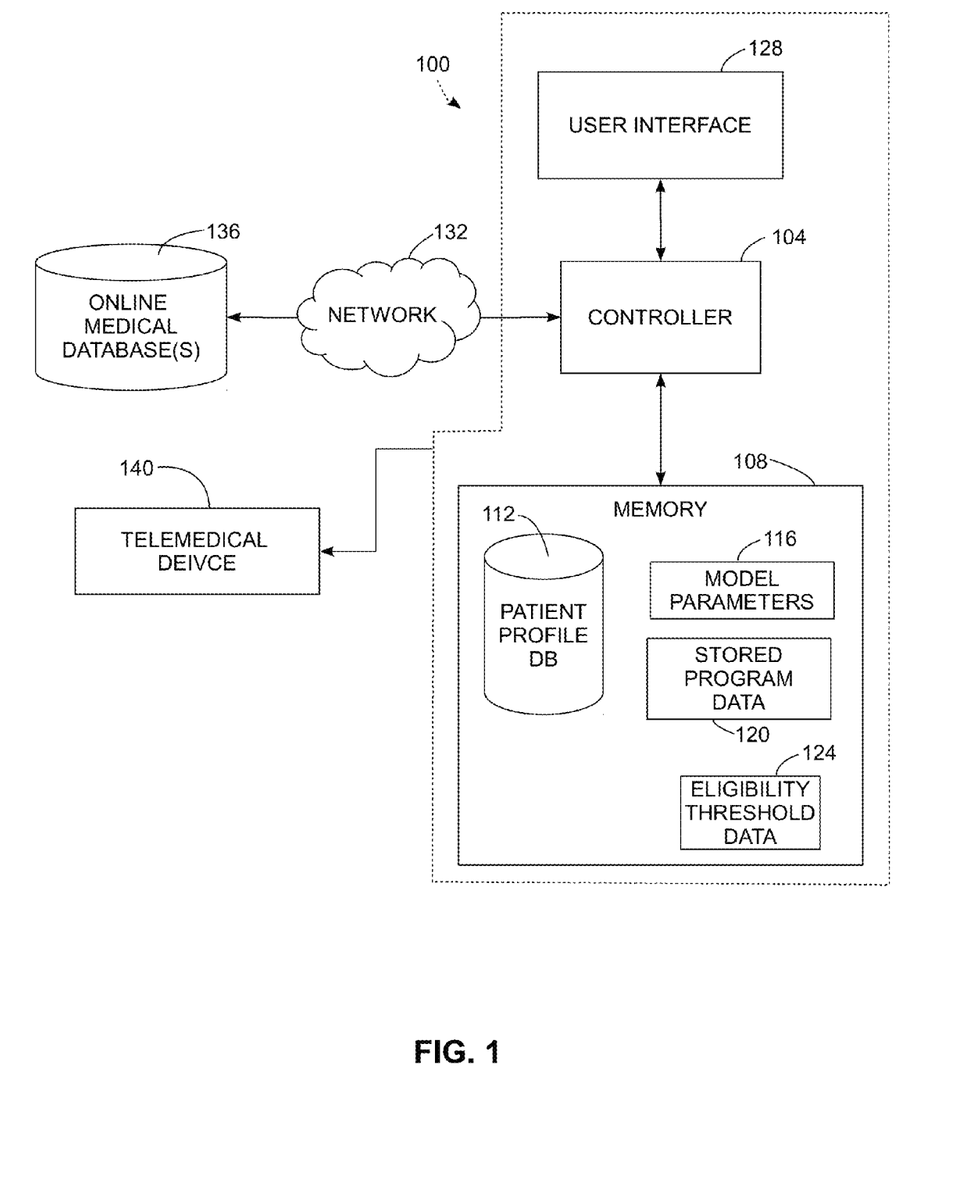
FIG. 1 is a schematic diagram of a patient information management system that is configured to identify patients for a telemedicine treatment regime.

FIG. 1 depicts a medical information system 100 that is configured to identify eligible recipients to receive a telemedical device. The system 100 includes a controller 104, memory 108, and a user interface 128. The memory 108 stores a patient profile database 112, parameters for a probabilistic model 116, stored program data 120, and threshold data 124 for determining the eligibility of a patient to receive a medical device.

In the system 100, the controller 104 is an electronic processing device such as a microcontroller, application specific integrated circuit (ASIC), field programmable gate array (FPGA), microprocessor including microprocessors from the x86 and ARM families, or any electronic device that is configured with programmed instructions and electronic components to perform the functions of the system 100 described herein. In an exemplary embodiment, the system 100 is a workstation with the controller 104 being a microprocessor implementing a version of the x86 or ARM microarchitecture that is configured to run a general purpose operating system. The memory 108 includes one or more data storage devices including volatile data storage devices, such as random access memory (RAM), and non-volatile data storage devices, which include solid state storage devices, magnetic disk drives, optical disk drives, and the like. The controller 104 is communicatively coupled to the memory 108 to enable the controller 104 to obtain data that are stored in the memory 108 and to store data in the memory 108. The controller 104 executes programmed instructions that are obtained from the stored program data 120 in the memory 108 to perform the processes described herein.

The memory 108 holds the patient profile database 112. The patient profile database stores medical data associated with each patient that is monitored by the system 100. In various embodiments, the patient profile database is implemented as a relational database, a key-value store, one or more files holding comma separated value (CSV) data, an object-oriented database, a hierarchical database, or any data storage scheme that enables the system 100 to store and retrieve medical data for one or more patients.

Figure 5:
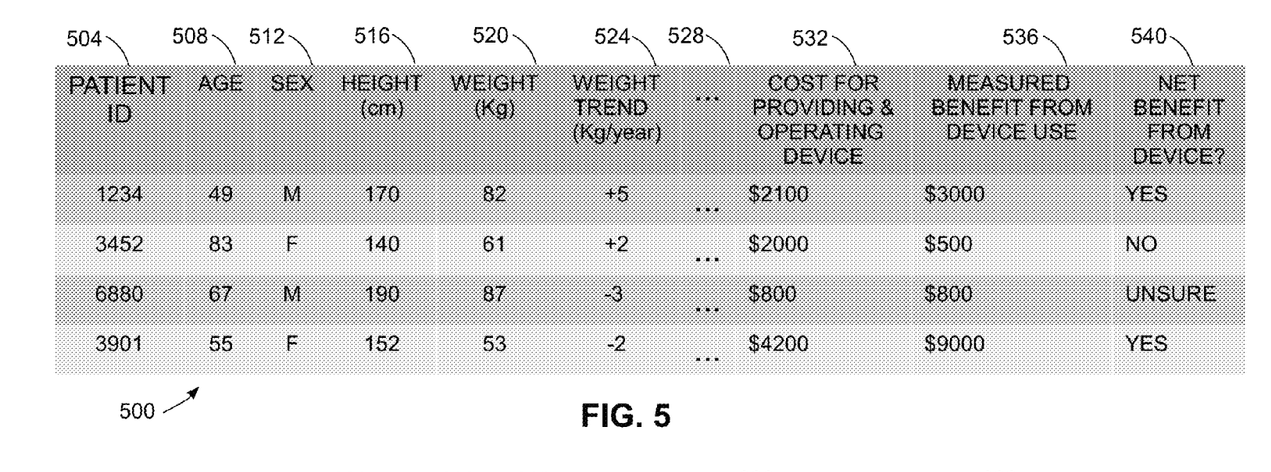
FIG. 5 is a sample representation of a patient profile database containing medical data for a plurality of patients.

FIG. 5 depicts one arrangement of medical data stored in the patient profile database 112. The medical data are arranged in a tabular format where each row contains medical data for a single patient and each column or field contains one data item for each of the patients. An intersection between a row and a field contains a single datum holding one medical datum for a single patient. FIG. 5 depicts a database table 500 that stores a patient ID 504, age 508, sex 512, height 516, weight 520, and weight trend 524 for each of four patients. The patients are identified by the numeric patient ID 504 along with the corresponding medical data recorded for each patient. Of course, data field 504-524 are merely exemplary, and various embodiments of the table 500 include different or additional fields that store medical data as indicated by the additional fields 528. Common examples of medical data include the names of one or more medications that the patient consumes, lists of previous medical procedures that the patient has undergone, and any diagnosed medical conditions affecting the patient. For example, in a telemedicine application for monitoring cardiac patients, any heart surgeries or prescriptions for medications to lower cholesterol form relevant patient data. The medical industry employs various standardized codes for some or all of the fields in the patient profile database that enable the system 100 to access electronic medical data such as one or more of the online medical database 136 to obtain medical data for the patient profile database 112.

In addition to medical data pertaining to each patient, the patient profile database 112 includes data associated with the costs and benefits of providing a telemedical device to each patient. Table 500 stores a record of the total cost 532 to provide the telemedical device to each patient, a measurement of the benefit 536 that the telemedical device provides to the patient, and an overall indicator of net benefit 540 provided by the telemedical device. The term "net benefit" as used herein refers a difference between the measured benefit 536 and the total cost 532. A positive net benefit occurs when the measured benefits exceed the total costs, and a negative net benefit occurs when the total costs exceed the measured benefits. The total cost 532 includes both the initial cost of the telemedical device, as well as the ongoing costs of monitoring medical data received from the telemedical device and providing telemedicine to the patient. The measured benefit 536 can include various factors such as savings realized from reducing the number of hospital visits or medical procedures that a patient undergoes because the patient receives telemedicine.

While the table 500 depicts the costs and benefits in monetary terms, alternative embodiments measure costs and benefits using other indicators. One alternative embodiment measures the cost of the telemedicine treatment in an expected benefit of a different treatment regime compared to the actual measured benefit of the telemedicine treatment. For example, a patient with high cholesterol could be placed on a regimen of statin drugs with occasional doctor visits to produce an expected reduction in the cholesterol level of the patient. If a telemedicine treatment with more frequent interaction with the doctor results in a larger reduction in the cholesterol level, then the benefit of the telemedicine treatment outweighs the "cost" measured for the traditional treatment option.

Referring again to FIG. 1, the controller 104 is further configured to operate a user interface 128. The user interface can include both input and output (I/O) devices. Input devices include, but are not limited to, a keyboard, mouse, touchscreen, voice input, and pen input device. Output devices include, but are not limited to, visual displays including visual displays that depict a graphical user interface (GUI), audible output, and various printing devices. The user interface 128 can be used to enter commands to control the operation of the system 100. In one configuration, an operator enters medical data corresponding to one or more patients via the user interface 128 for storage in the patient profile database 112.

In the embodiment of FIG. 1, the controller 104 is configured to interface with a data network 132 including a local area network (LAN) and/or a wide area network (WAN) such as the Internet. The data network 132 enables the system 100 to receive medical data from one or more data sources depicted in FIG. 1 as medical databases 136. The medical databases 136 can hold personal health records for one or more patients in an electronic format. The system 100 is configured to receive medical records corresponding to a new or existing patient and store some or all of the medical data in the medical records in the patient profile database 112.

Figure 2:
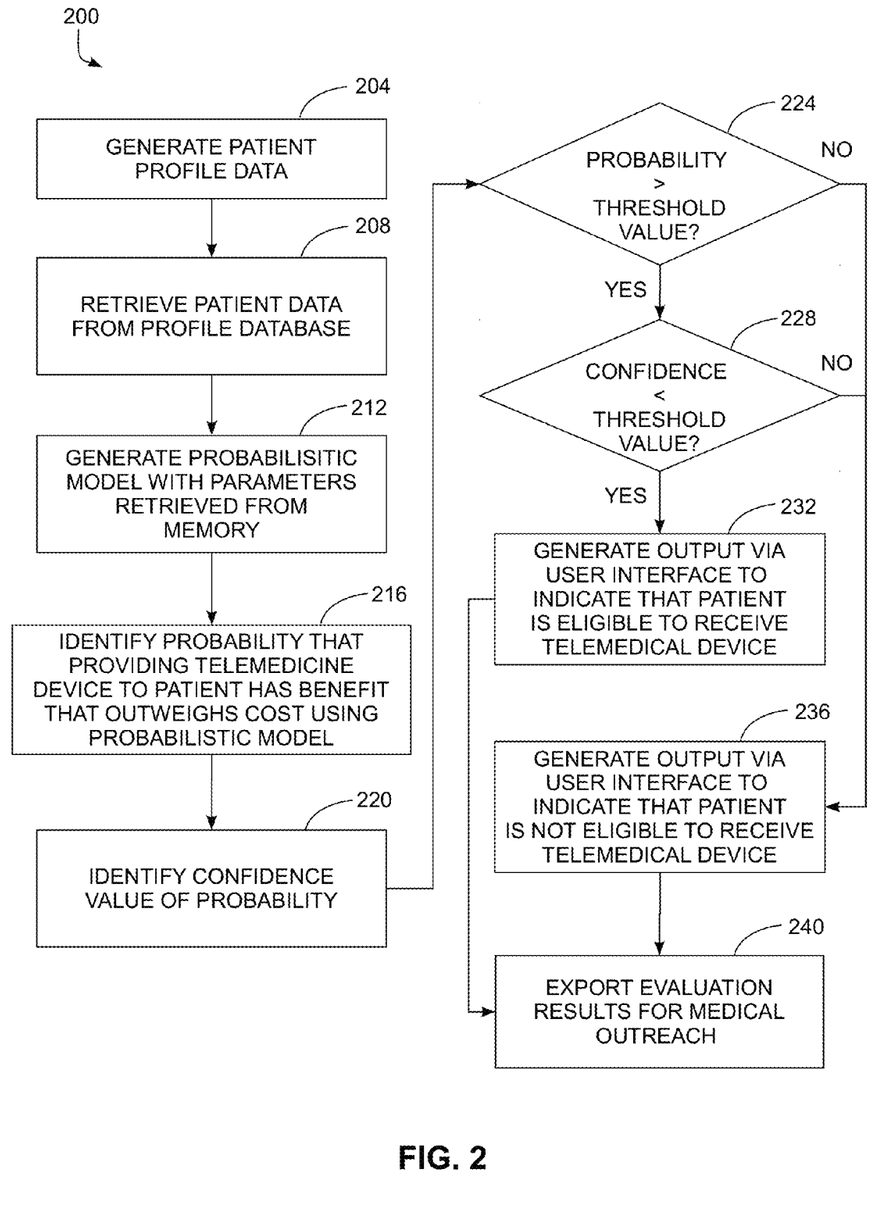
FIG. 2 is a block diagram of a process for identifying whether a patient is eligible to receive a telemedical device.

FIG. 2 depicts a process 200 for selecting recipients of a telemedical device. The process is implemented with the system 100, for example, as the controller 104 executes programmed instructions to operate the components of the system. Process 200 begins by generating a patient profile data (block 204). Patient profile data include medical data from one or more medical records pertaining to a patient. The patient profile data can be generated for a new patient, or for an existing patient when additional medical data become available. The system 100 is configured to access the network 132 to receive medical data from one or more online medical databases 136. Examples of online medical database include electronic health records, hospital records, pharmacy records, medical test results, and any other source of medical data about the patient. The patient or a healthcare provider can optionally provide medical data using the user interface 128.

Figure 6:
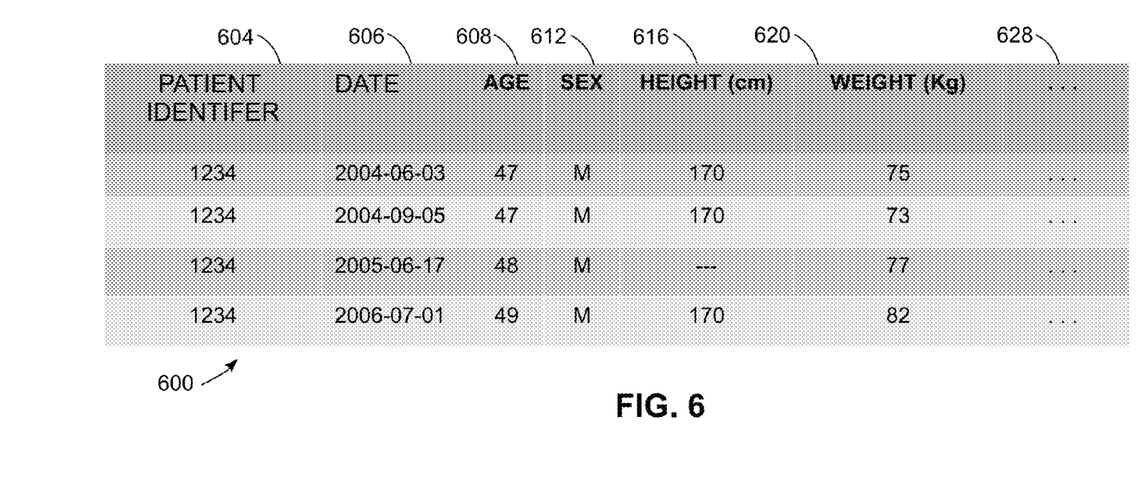
FIG. 6 is a sample representation of patient medical data for a patient who is a candidate to receive a telemedical device.

The system 100 is configured to store medical data for each patient in the patient profile database 112. FIG. 5 and FIG. 6 depict medical data as stored in the profile database 112. FIG. 5 depicts a table 500 with medical data for a plurality of patients in conjunction with measured costs 532 and benefits 536 associated with the treatment of each patient. FIG. 5 includes a patient identification number 504, age 508, sex 512, height 516, weight 520, and weight trend 524 for each patient. Various other medical data that are relevant to the treatment can be stored and are represented as fields 528 in FIG. 5.

FIG. 6 depicts a table 600 including multiple sets of medical data stored for a single one of the patients 1234 depicted in FIG. 5. FIG. 6 includes the patient identification number 604, age 608, sex 612, height 616, and weight 620 data depicted in FIG. 5, along with additional medical data 628. Each row in the table 600 is a subset of the total medical data for the patient collected at a date 606 in the medical history of the patient. For example, the patient undergoes a medical test or data is collected during an appointment with a doctor on a particular date, and the medical data generated for the patient are recorded and stored in the table 600. Certain records may include empty fields such as the height field 616 for the medical record corresponding to Jun. 17, 2005. Some data held in table 600 can generate trends corresponding to changes in the health of the patient. For example, changes in the weight field 620 over time can generate a trend showing weight gain or weight loss. The data in the table 500 are generated from one or more medical records held in the table 600. For some medical data like age and weight, the most recently recorded medical data from the table 600 are used directly in the table 500. Other fields in the table 500, such as the weight trend field 524, are generated by measuring changes over time between two or more different sets of medical data from the table 600 to establish trends.

Referring again to FIG. 2, process 200 retrieves the generated patient data from the patient profile database (block 208). In the system 100, the controller 104 is configured to retrieve data corresponding to a selected patient from the patient profile database 112. In the embodiment of system 100, the controller 104 retrieves the medical data in table 500 from fields 504-528 for a single patient. The values in table 500 include an identified cost for providing and operating the device 532, measured benefit from the medical device 536, and an indicator of whether the telemedical device has provided a measured benefit that is greater than the cost 540. In the case of a new patient, the fields 532-540 are unknown and process 200 generates a probability to predict whether the patient will benefit from telemedicine delivered with reference to the telemedical device.

Process 200 continues by generating a probabilistic model with a plurality of model parameters retrieved from memory (block 212). In the system 100, the controller 104 retrieves the model parameters 116 from the memory 108, and stored program instructions 120 include instructions that enable the controller 104 to generate the probabilistic model. In one embodiment, the controller 104 generates a probabilistic model that is a logistic regression model having the following formula:

$$P(C \mid f, \theta) = \frac{1}{1 + e^{-f\theta}}$$

where C is a classification associated with the patient given a plurality of f features, also referred to as a feature vector f. Each feature in the feature vector f corresponds to one medical datum associated with one patient. The probabilistic model also includes a plurality of model parameters arranged in a model parameter vector $\theta$. Each of the model parameters in the model parameter vector $\theta$ represents a relative numeric weighting assigned to a corresponding one of the features in the feature vector f. The classification C corresponds to a decision that the patient will receive a benefit from the telemedical device that is greater than a cost associated with the telemedical device. A second classification $P(\overline{C} \mid f, \theta)$ corresponds to a decision that the patient will not receive a benefit from the telemedical device that outweighs the cost, and is defined as $1 - P(C \mid f, \theta)$.

In the system 100, each feature in the feature vector f corresponds to a single medical datum for the patient such as each of the fields 508-528 in FIG. 5. In one embodiment, the model parameters $\theta$ include a vector of signed numeric values that assign a weight to each medical datum for the features of the feature vector f for the patient. The absolute value assigned to each parameter selects a relative weight for the corresponding medical datum, with larger absolute values corresponding to larger relative weights. The sign of the each of the model parameters in the model parameter vector $\theta$ indicates whether the parameter increases or decreases the probability of the assigning the classifier C. For example, in FIG. 5, a negative value of a model parameter for the weight trend datum 524 indicates that increases and decreases in weight of the patient lower and raise, respectively, the likelihood that the patient receives a net benefit from the telemedical device.

Figure 7:
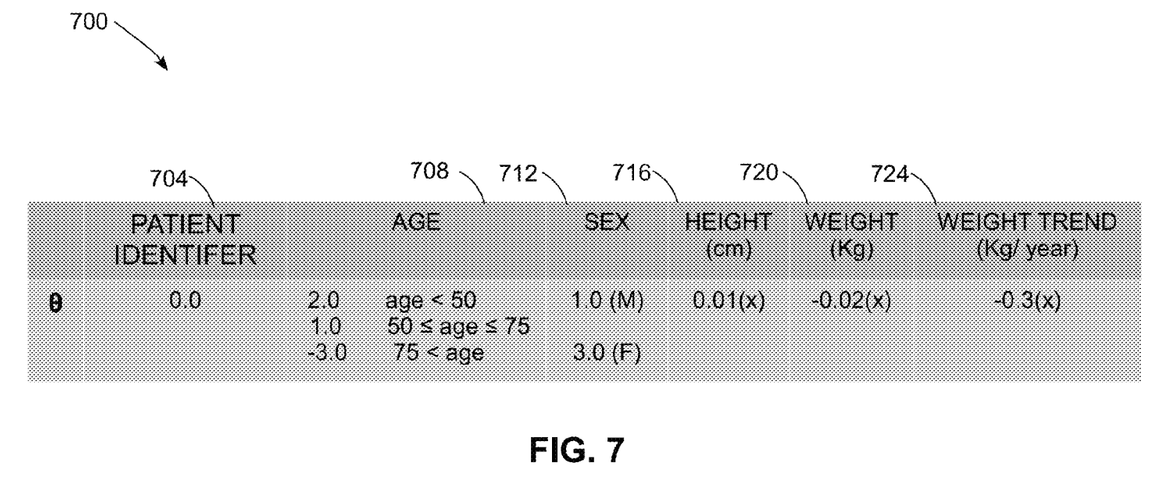
FIG. 7 is an exemplary depiction of parameters for probabilistic model that are generated from patient profile data.

FIG. 7 depicts example model parameters 700 corresponding to the fields 508-524 in FIG. 5. For some model parameters and corresponding medical data, a numeric value of the medical datum is multiplied by the parameter value to produce to a numeric value for the logistic regression. In FIG. 7, the height parameter 716, weight parameter 720, and weight trend parameter 724 are each assigned a numeric value that is multiplied by the numeric value of the datum when applying the logistic regression. For example, a patient that is 165 cm tall has a total height value of 1.65 using the height parameter value of 0.01. Other medical data are assigned a parametric value using a piecewise function. The age parameter 708 includes three distinct values for patients below the age of 50, between 50 and 75, and above 75. In the case of FIG. 7, patients under 50 have a larger probability of a net benefit than patients between 50 and 75, while patients above the age of 75 are less likely to receive a net benefit from the telemedical device. Non-numeric medical data can be assigned to selected values based on the value of the parameter. For example, the sex datum 712 has male and female values that are non-numeric. In FIG. 7, the female parameter is selected to have a value of 3.0 and the male parameter is selected to have a value of 1.0, indicating that females have a relatively greater probability of receiving a net benefit from the telemedical device. Certain medical data can also be ignored, such as the patient ID 704 that receives a parameter value of 0 and is ignored when performing the logistic regression function on the medical data for the patient.

Using the logistic regression with medical data features f for the example patient 1234 in FIG. 5 and the model parameters θ in FIG. 7 results in:

$$P(C \mid f, \theta) = \frac{1}{1 + e^{-(age+sex+height+weight+weight\ trend)}}$$
$$= \frac{1}{1 + e^{-(2+1+1.7-1.64-1.5)}}$$
$$\approx 0.82$$

The value corresponds to an 82% chance that patient 1234 receives a net benefit from the telemedical device. The logistic regression predicts an 18% chance that the patient does not receive a net benefit from the telemedical device.

Process 200 continues by generating an optional confidence value corresponding to the generated probability (block 220). In the system 100, the processor 104 is configured to generate a confidence value. The confidence value represents an estimate of the level of certainty of the probability value. In one embodiment, the confidence is related to the value of the identified probability using an entropy measurement according to the following equation: $H(C|f) = -(P(C|f, \theta) \log(P(C|f, \theta)) + P(\overline{C}|f, \theta) \log(P(\overline{C}|f, \theta)))$. Lower values of entropy indicate a greater confidence in the probability generated by the logistic regression. Using the example probability generated above, the entropy is: $H(C|f) = (-0.82 \log(0.82) + 0.18 \log(0.18)) \approx 0.2$.

Another method for identifying the confidence value includes generation of a confidence value that corresponds to a sum of multiple disagreement values of model parameters used to identify the probability in the logistic regression. First, a plurality of parameter vectors $\theta_N$, are generated by N different classifier functions, also referred to as a committee of classifiers. The N classifier functions generate the $\theta_N$ parameter vectors from a predetermined set of training data D. The training data D include one or more sets of feature vectors that include the same medical data in the feature vector f corresponding to a single patient who is undergoing evaluation for the telemedical device. In one embodiment, the training data D include medical data and predetermined results for a group of patients who have already received telemedical treatment. The following confidence equation identifies a confidence value with reference to differences in the regression values generated by the individual parameter vectors $\theta_N$ conditioned on the identified medical data feature vector f of a single patient:

$$\text{Confidence}(C|f) = \int_{\theta_1} \int_{\theta_2} |P(C|f,\theta_1) - P(C|f,\theta_2)| P(\theta_1|D) P(\theta_2|D) d\theta_1 d\theta_2.$$

In the confidence value equation, $\theta_1$ and $\theta_2$ represent pairs of model parameter vectors generated by the N classifiers without regard to the order of the classifiers. For an example with three classifiers A, B, and C, the pairs of parameter vectors are $(\theta_A, \theta_B)$, $(\theta_A, \theta_C)$, and $(\theta_B, \theta_C)$. The values for $P(C|f,\theta_1)$ and $P(C|f,\theta_2)$ represent the regression value for a single patient using two different sets of classifier model parameters $\theta_1$ and $\theta_2$.

The difference between the values of $P(C|f,\theta_1)$ and $P(C|f,\theta_2)$ are multiplied by two scaling factors $P(\theta_1|D)$ and $P(\theta_2|D)$ for each pair of parameter vectors $\theta_1$ and $\theta_2$. As used herein, the term "scaling factor" refers to the conditional probability of generating the parameter vectors $\theta_1$ and $\theta_2$ given the training data D for each of the N classifier functions. The scaling factors $P(\theta_1|D)$ and $P(\theta_2|D)$ identify the significance assigned to differences between the regressions for the parameter vectors $\theta_1$ and $\theta_2$ in the in the confidence equation.

The difference between values generated by the classifiers using the different model parameter vectors with a single set of medical data f for one patient corresponds to a disagreement value. The confidence value equation generates a sum of all the disagreement values-between each model parameter vector given the medical data f for one patient. For example, if model parameter vector $\theta_1 = [1, 2.4, 3.3, -5.1]$ and model parameter vector $\theta_2 = [1, 2, 4, 3.3, -1.8]$, the disagreement in the regressions $P(C|f,\theta_1)$ and $P(C|f,\theta_2)$ for given medical data f corresponds to the difference in the final parameter in $\theta_1$ and $\theta_2$. The magnitude of the confidence value indicates a level of disagreement between predictions generated by different model parameters. Smaller disagreement values indicate that the probability values generated by different model parameters and features produce similar probabilities.

Process 200 continues to identify the eligibility of the patient to receive a telemedical device using the probability value and optional confidence value. Process 200 compares the probability value from the logistic regression to a predetermined threshold value (block 224). In the system 100, a predetermined threshold value 124 is stored in the memory 108 and the controller 104 compares the generated probability value to the predetermined threshold. The threshold value is selected based on various criteria, such as the overall number of devices that are available for use by patients and the level of importance of the telemedicine compared to other medical treatment options, for example. Other or additional criteria are used in other embodiments to select predetermined threshold values used by the probabilistic model.

If process 200 generates a confidence value, then the confidence value is compared to a predetermined confidence threshold value as well (block 228). In the embodiments described above, a low numeric value indicates a higher confidence level, so the identified confidence level passes when the confidence value is less than the predetermined confidence threshold value. Other measures of confidence can be configured to exceed a predetermined threshold value as well. In the system 100, the predetermined confidence threshold value is stored in the eligibility threshold data 124 in the memory 108.

When a patient has a sufficiently high predicted probability of receiving a net benefit from the telemedical device, and an optional confidence level of the prediction meets the predetermined threshold, process 200 concludes by generating a signal via the user interface to indicate that the patient is eligible to receive a telemedical device (block 232). In some embodiments, the output is a graphical symbol with accompanying text that informs the healthcare provider to begin treatment with the telemedical device. In the system 100, the user interface 128 is configured to display a message indicating that the patient is eligible to receive a telemedical device. In the event that a patient is not eligible to receive the telemedical device, the user interface outputs a second message indicating that the patient is not eligible to receive the telemedical device (block 236). When a patient is not eligible to receive a telemedical device, the system 100 is configured to display another course of treatment that is more suited to the needs of the patient based on the patient data.

In an alternative embodiment, the system 100 is further configured to transfer program and configuration data to the telemedical device when a user is eligible to receive the device. In FIG. 1, the controller 104 programs a telemedical device 140. The telemedical device 140 is connected to the system 100 via a universal serial bus (USB) interface, wireless or wired network interface, or any other data transfer interface that enables the system 100 to program the telemedical device 140 and to provide the telemedical device 140 to the patient. The telemedical device 140 receives configuration data that corresponds to the medical data of the patient. For example, if the patient is hypertensive, the telemedical device 140 can receive configuration data to obtain blood pressure measurements by prompting the patient to enter blood pressure measurements or by receiving data directly from a sphygmomanometer.

In an optional embodiment, process 200 exports the results of the patient evaluation for use with medical outreach (block 240). For example, selected portions of the medical data for patients and the evaluations of process 200 can be sent via a data network, such as the Internet, to a database maintained by one or more healthcare providers. In the example of FIG. 1, the system 100 transmits the results of process 200 indicting whether the patient is eligible to receive the telemedical device to the online medical databases 136. The exported medical data help identify characteristics of patients who have a high likelihood of benefiting from telemedical treatment. A patient outreach service can contact healthcare providers and potential patients who can benefit from telemedical treatment. Some embodiments use the exported results of large groups of patients to improve the accuracy of process 200.

Figure 3:
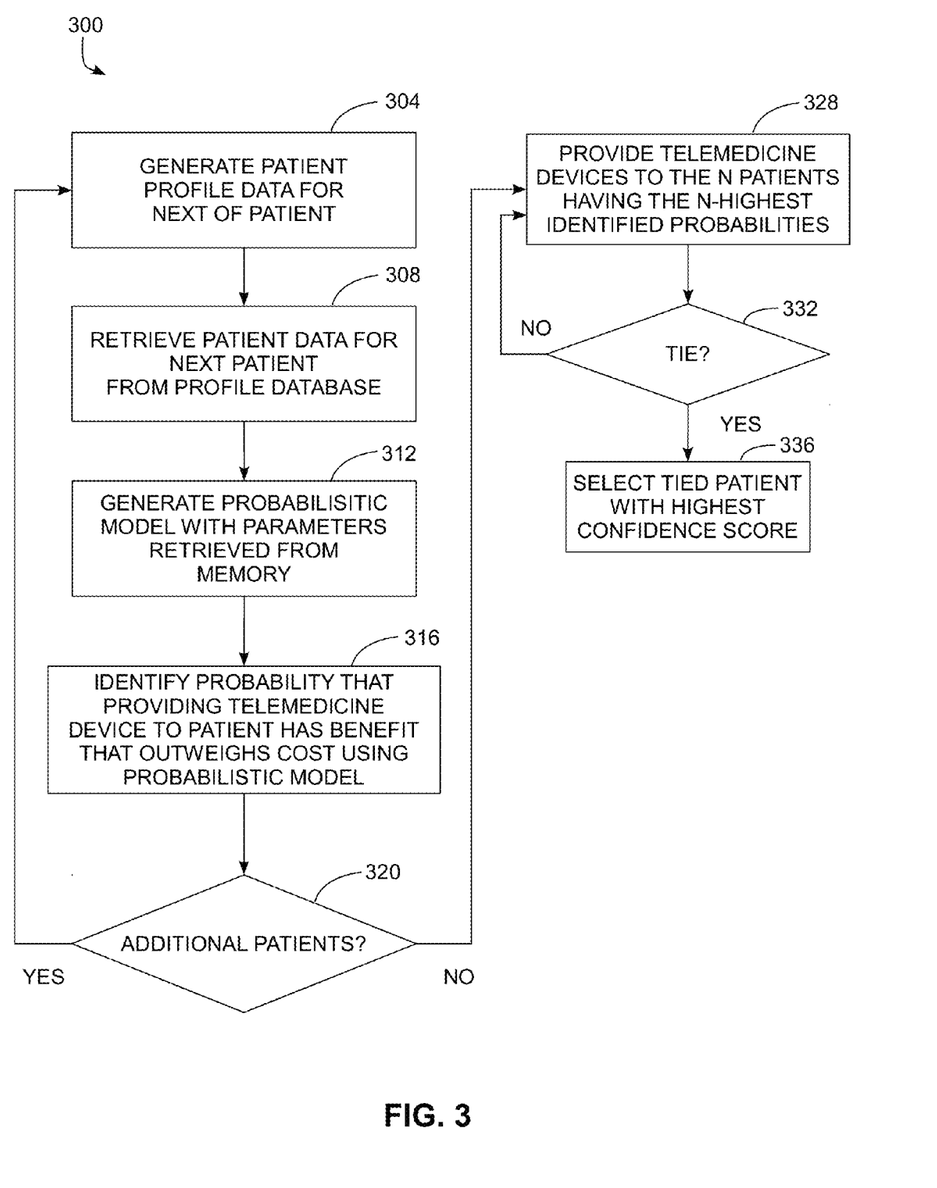
FIG. 3 is a block diagram of another process for identifying selecting a group of patients to receive telemedical devices.

FIG. 3 depicts a process 300 for identifying a plurality of recipients for a telemedical device. Process 300 is described in conjunction with system 100 of FIG. 1 by way of example. The process 300 is implemented by a processor executing programmed instructions in a system, such as system 100, to decide which subgroup of patients in a group of patients should receive a limited number of telemedical devices. For example, the system 100 can accommodate three additional patients, but five patients apply for the telemedical treatment. Process 300 provides a method for selecting the patients to receive the telemedical device.

Process 300 begins by generating medical profile data for one patient in the group of patients who are applying to receive a telemedical device (block 304). Process 300 continues by retrieving the medical data for the one patient from the profile database 112 (block 308), generating the probabilistic model using the model parameters 116 stored in the memory 108 (block 312), and identifying a probability that the one patient will receive a net benefit from treatment with the telemedical device (block 316). In the system 100, the controller 104 is configured to perform process blocks 304-316 in substantially the same manner as process blocks 204-216, respectively, in process 200.

Process 300 repeats blocks 304-316 for each patient in the group of patients who have applied to receive the telemedical device (block 320). Once a probability is identified for each of the patients, the N patients having the highest probabilities of a net benefit are each selected to receive one of N telemedical devices (block 328). The number N can be selected based on the number of available telemedical devices or on the available patient capacity of a healthcare provider. A tie occurs (block 332) when multiple patients have the same or a similar net benefit probability. Process 300 breaks a tie by identifying the confidence value of each patient, and selecting the patient with the highest confidence, or the lowest numeric entropy or disagreement value identified in process 200, to receive the telemedical device.

Figure 4:
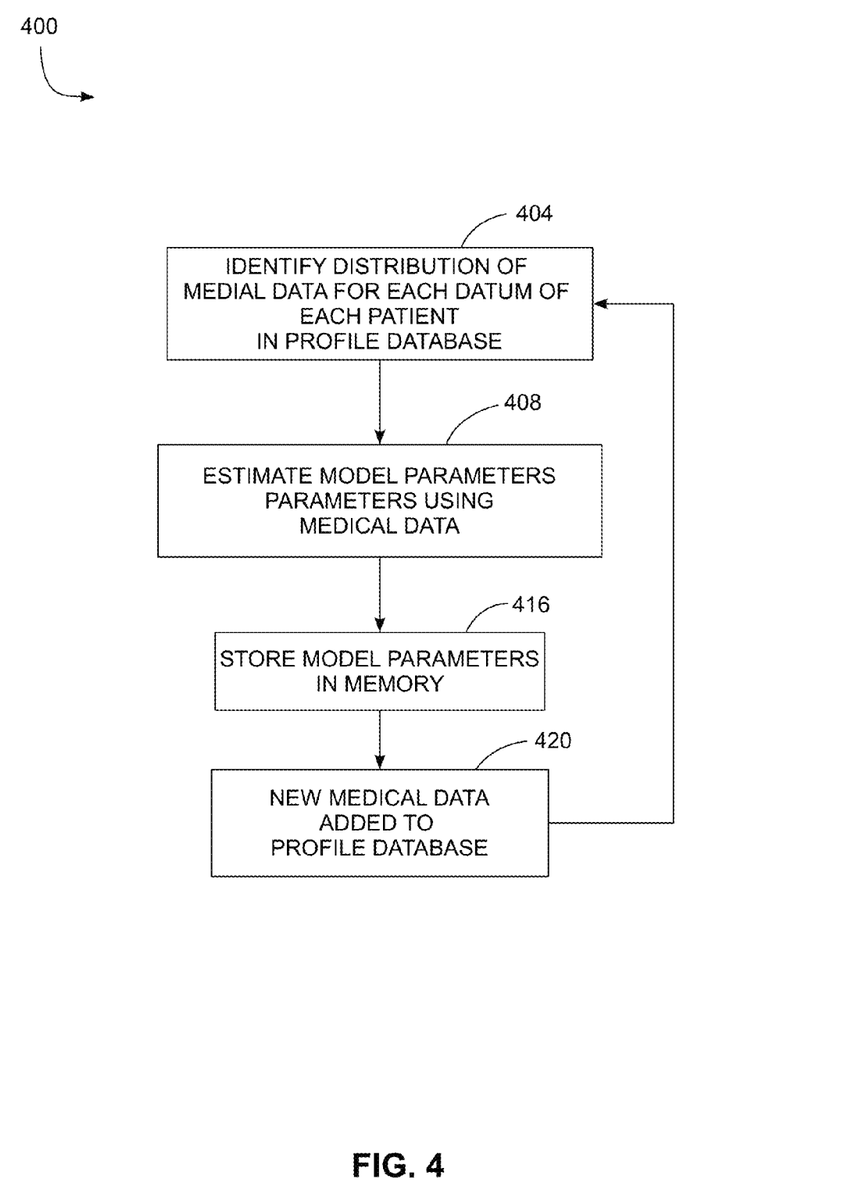
FIG. 4 is a block diagram of a process for generating parameters for a probabilistic model that is used to select patients to receive a telemedical device using recorded data from a plurality of existing patients.

As described above, processes 200 and 300 use a logistic regression probabilistic model with model parameter vector $\theta$ to identify recipients of a telemedical device. FIG. 4 depicts a process 400 for generation of the model parameters in the model parameter vector $\theta$. In one embodiment, process 400 generates a plurality of model parameters that correspond to each datum in the medical data used to perform the logistic regression. Process 400 is described in conjunction with system 100 of FIG. 1 by way of example. Process 400 begins by identifying a distribution of data for one datum of each patient in the medical profile data (block 404). In the system 100, each medical datum value in the patient profile database 112 is used by a system, such as system 100, to generate one of the parameter values. As depicted in FIG. 5, each of the fields 508-528 holds data corresponding to a single type of datum in the patient profile database. The particular form of the distribution varies depending upon the types of values representing each medical datum. For example, the height datum 512 and weight datum 520 follow a numeric distribution that may be a Gaussian distribution for certain groups of patients. The sex datum 512 only contains two values for male and female. The weight trend datum 524 contains both positive and negative numbers to indicate the patient has gained or lost weight over time.

Once the distribution for the selected datum is determined, process 400 generates a parameter estimator to estimate parameter values of a probabilistic model, such as the logistic regression parameters, given the observed benefits of the device as depicted in field 540 of FIG. 5 (block 408). In one embodiment, an iteratively reweighted least squares (IRLS) method generates numeric parameter values from the medical data using a maximum likelihood estimation technique. Alternative embodiments use other estimation techniques including Bayesian classifiers. In the patient profile database 112, the identified net benefit of the telemedical device for each patient, depicted as field 540 in FIG. 5 is an observed outcome of medical treatment received by each of the patients. The estimator generates a model parameter for each medical datum 508-528 that maximizes the likelihood of the observed net benefit. In the system 100, the controller 104 generates the model parameters using stored program instructions retrieved from the stored program data 120.

Process 400 generates numeric model parameters for some numeric data types that have a linear relationship to the probability of a net benefit. In FIG. 7, the height parameter 716, weight parameter 720, and weight trend parameter 724 are each assigned a numeric value that is multiplied by the numeric value of the datum when applying the logistic regression.

For some types of patient data the estimator considers patients with similar data values as a group to generate parameters. In one configuration, all patients in an age group of 40-50 years can be treated as having a single age for purposes of the estimating the model parameters. Additionally, a piecewise parameter generation can be useful for some datum types. One piecewise parameter is generated based on age ranges of patients. For patients below the age of 50 a positive parameter indicates that the telemedical device has a constant positive result for all patients in the age range. The parameter value is still positive, but with a smaller value, for patients between the ages of 50 and 75. The parameter is negative for patients over the age of 75 indicating that advanced age tends to reduce the likelihood that the telemedical device will benefit such patients.

Some model parameters have a non-numeric value including the sex parameter 512. Other non-numeric medical data include names of medications prescribed to the patient and surgical procedures performed on the patient. Process 400 generates numeric model parameters for the non-numeric medical data using the parameter estimator. FIG. 7 depicts an example set of model parameters 704-720 that correspond to the medical data fields 504-524 depicted in FIG. 5, respectively.

As depicted in FIG. 5, some patients, such as patient 6880, do not have a known net benefit for the telemedical device due to the unavailability of cost and benefit data to determine a net benefit. In some configurations, the process 400 ignores medical data from these patients when generating model parameters. The processor 104 also applies one or more filters to the medical data to reduce or eliminate the effects of inaccurate or noisy data on the parameter generation. For example, some medical data, such as weight, may be subject to fluctuations that are not represented in the medical records for a patient. The noisy data may be filtered prior to providing the data to the parameter estimator, or the parameter estimator can be configured to discount a noisy range of values for a medical datum when generating the parameters.

Referring again to FIG. 4, the process 400 stores the generated parameter values in memory (block 416). In the system 100, the processor 104 stores the generated parameter values as model parameters 116 in the memory 108. The stored model parameters 116 are available for later use with processes 200 and 300. During operation, new medical data are added to the medical profile database as new patients receive treatment and new medical data are generated for existing patients (block 420). Process 400 returns to block 404 to generate updated model parameters as additional medical data are added to the medical profile database 112. As the system 100 monitors an increasing number of patients, the volume of medical data used to generate the model parameters increases. The accuracy of recommendations regarding the cost to benefit ratio of telemedical devices increases as more patients undergo telemedical treatment and provide additional medical data to the patient profile database 112.

It will be appreciated that variants of the above-described and other features and functions, or alternatives thereof, may be desirably combined into many other different systems, applications or methods. Various presently unforeseen or unanticipated alternatives, modifications, variations or improvements may be subsequently made by those skilled in the art that are also intended to be encompassed by the following claims.

What is claimed:

1. A method for selecting recipients of a medical device comprising:
   providing first medical data associated with one patient from a database stored in a memory to a controller communicatively coupled to the memory;
   identifying with the controller a probability that a medical device provides a medical benefit to the one patient that exceeds a cost associated with providing the medical device to the one patient with reference to the first medical data and a probabilistic model, the probabilistic model having a plurality of model parameters stored in the memory and provided to the controller, each model parameter corresponding to one type of datum in the first medical data;
   identifying a confidence value corresponding to the identified probability with the controller, the confidence value being identified by:
      identifying a difference between a first probability value generated by the probabilistic model using the first medical data and a first plurality of model parameters and a second probability value generated by the probabilistic model using the first medical data and a second plurality of model parameters with the controller;
      identifying a first scaling factor of the first plurality of model parameters with reference to the probabilistic model and a plurality of predetermined training data with the controller;
      identifying a second scaling factor of the second plurality of model parameters with reference to the probabilistic model and the plurality of predetermined training data with the controller; and
      identifying the confidence value with reference to the identified difference, the first scaling factor, and the second scaling factor with the controller; and
   generating with the controller and a user interface device that is communicatively coupled to the controller an output indicating the one patient is eligible to receive the medical device, the output being generated in response to the identified probability exceeding a first predetermined probability threshold value stored in the memory and the confidence value being below a second predetermined threshold stored in the memory.

2. The method of claim 1, further comprising:
   transmitting with the controller data corresponding to the identified probability that the medical device provides the medical benefit to the one patient that exceeds the cost associated with providing the medical device to the one patient to a medical database via a data network.

3. The method of claim 1, the first medical data further comprising:
   a first medical data subset corresponding to the one patient at a first time; and
   a second medical data subset corresponding to the one patient at a second time, the second time being later than the first time, the probability being identified by the controller with reference to a difference between at least one datum in the first medical data subset and at least one corresponding datum in the second medical data subset.

4. The method of claim 1, the confidence value being an entropy value generated by the controller with reference to the classification probability.

5. The method of claim 1, further comprising:
   storing programmed instructions in the memory corresponding to a logistic regression probabilistic model; and identifying with the controller the probability that the medical device provides the medical benefit to the one patient that exceeds the cost associated with providing the medical device to the one patient with reference to the first medical data and the logistic regression model.

6. The method of claim 1 further comprising generating the plurality of model parameters with the controller and storing the generated plurality of model parameters in the memory with reference to medical data corresponding to a plurality of patients stored in the database, the medical data corresponding to the plurality of patients including a plurality of values corresponding to each datum in the first medical data.

7. The method of claim 1, the first medical data including a datum corresponding to at least one of an age, sex, height, weight, medications, previous medical procedure, and diagnosed medical condition of the patient.

8. The method of claim 1, the medical device being a device configured to provide additional medical data corresponding to the one patient to the database.

9. The method of claim 1 further comprising:
providing a plurality of medical data associated with a plurality of patients from the database in the memory to the controller;
identifying with the controller a plurality of probabilities that the medical device provides a medical benefit to each of the plurality of patients that exceeds a cost associated with providing the medical device to each of the plurality of patients with reference to the plurality of medical data and the probabilistic model; and
generating with the controller and the user interface device an output indicating each of a selected group of the plurality of the patients is eligible to receive one of a first number of the medical device, the controller and user interface device generating the output for the selected group of the plurality of patients having identified probabilities that are greater than identified probabilities of a remaining group of the plurality of patients.

10. A system for controlling distribution of medical devices to patients comprising:
a user interface device;
a memory configured to store:
a database containing medical data corresponding to a plurality of patients;
a plurality model parameters corresponding to a probabilistic model, each model parameter corresponding to one type of datum in the plurality of medical data; and
a plurality of stored program instructions; and
a controller operatively connected to the user interface device and the memory, the controller being configured to execute the stored program instructions to:
retrieve first medical data corresponding to one patient from the database;
identify a probability that a medical device provides a medical benefit to the one patient that exceeds a cost associated with providing the medical device to the one patient with reference to the first medical data and the probabilistic model having the plurality of model parameters;
identify a difference between a first probability value generated by the probabilistic model using the first medical data and a first plurality of model parameters and a second probability value generated by the probabilistic model using the first medical data and a second plurality of model parameters;
identify a first scaling factor of the first plurality of model parameters with reference to the probabilistic model and a plurality of predetermined training data;
identify a second scaling factor of the second plurality of model parameters with reference to the probabilistic model and the plurality of predetermined training data;
identify a confidence value corresponding to the identified probability with reference to the identified difference, the first scaling factor, and the second scaling factor; and
display an output via the user interface device to indicate provision of the medical device to the one patient in response to the identified probability exceeding a first predetermined threshold and being below a second predetermined threshold.

11. The system of claim 10, the controller being further configured to:
transmit data corresponding to the identified probability that the medical device provides the medical benefit to the one patient that exceeds the cost associated with providing the medical device to the one patient to a medical database via a data network.

12. The system of claim 10, the first medical data further comprising:
a first medical data subset corresponding to the one patient at a first time; and
a second medical data subset corresponding to the one patient at a second time, the second time being later than the first time, the controller being further configured to identify the probability with reference to a difference between at least one datum in the first medical data subset and at least one corresponding datum in the second medical data subset.

13. The system of claim 10, the confidence value being an entropy value generated with reference to the classification probability.

14. The system of claim 10, the probabilistic model being a logistic regression model.

15. The system of claim 10, the controller being further configured to generate the plurality of model parameters with reference to medical data corresponding to the plurality of patients stored in the database, the medical data corresponding to the plurality of patients including a plurality of values corresponding to each datum in the first medical data.

16. The system of claim 10, the first medical data including a datum corresponding to at least one of an age, sex, height, weight, medications, previous medical procedure, and diagnosed medical condition of the patient.

17. The system of claim 10, the medical device being a device configured to provide medical data corresponding to the one patient to the database.

18. The system of claim 10, the controller being further configured to:
retrieve a plurality of medical data associated with a plurality of patients from the database;
identify a plurality of probabilities that the medical device provides a medical benefit to each of the plurality of patients that exceeds a cost associated with providing the medical device to each of the plurality of patients with reference to the plurality of medical data and the probabilistic model; and
generate a list of identifiers corresponding to each of a selected group of the plurality of the patients via the user interface device, each patient in the selected group of patients being selected to receive one of a first number of the medical devices, the selected group of the plurality of patients having identified probabilities that are greater than identified probabilities of a remaining group of the plurality of patients.

\* \* \* \* \*